United States Patent
Qian

(10) Patent No.: US 7,214,726 B2
(45) Date of Patent: *May 8, 2007

(54) METHODS OF USING TWO-PART SELF-ADHERING DENTAL COMPOSITIONS

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 451 days.

This patent is subject to a terminal disclaimer.

(21) Appl. No.: 10/621,708

(22) Filed: Jul. 17, 2003

(65) Prior Publication Data

US 2005/0014861 A1    Jan. 20, 2005

(51) Int. Cl.
A61K 6/083 (2006.01)
A61C 5/09 (2006.01)
(52) U.S. Cl. ............... 523/116; 523/118; 433/228.1
(58) Field of Classification Search ........... 523/116, 523/118
See application file for complete search history.

(56) References Cited

U.S. PATENT DOCUMENTS

| | | | | |
|---|---|---|---|---|
| 3,991,008 | A | 11/1976 | Temin et al. | 260/42.15 |
| 4,569,976 | A | 2/1986 | Zimmerman et al. | 526/204 |
| 4,872,936 | A | 10/1989 | Engelbrecht | 156/307.3 |
| 5,063,257 | A | 11/1991 | Akahane et al. | 523/116 |
| 5,154,762 | A | 10/1992 | Mitra et al. | 106/35 |
| 6,127,451 | A | 10/2000 | Qian | 523/116 |
| 6,214,101 | B1 | 4/2001 | Nakaseko | 106/35 |
| 6,500,004 | B2 * | 12/2002 | Jensen et al. | 433/228.1 |
| 6,818,682 | B2 * | 11/2004 | Falsafi et al. | 523/116 |
| 2003/0134933 | A1 | 7/2003 | Jin et al. | |

FOREIGN PATENT DOCUMENTS

| | | |
|---|---|---|
| EP | 0923924 | 12/1998 |
| EP | 0948956 | 10/1999 |
| EP | 1479364 | 5/2004 |
| WO | WO 92/21314 | 12/1992 |
| WO | WO 02/O92023 | 11/2002 |
| WO | WO 03/057792 | 7/2003 |

OTHER PUBLICATIONS

EPO, *European Search Report*, EP 04254247, mailed Aug. 18, 2005, 3 pg.

3M ESPE, *RelyX Unicem Self-Adhesive Universal Resin Cement*, Technical Product Profile, 2002, pp. 1-40.
GC FujiCEM Reinforced Glass Ionomer Luting Cement, GC America, http://www.gcamerica.com/gcfujcem.html.

* cited by examiner

Primary Examiner—Tae H Yoon
(74) Attorney, Agent, or Firm—Wood, Herron & Evans, L.L.P.

(57) ABSTRACT

A method for providing a dental composition comprising providing a paste/paste two-part self-adhering dental composition comprising
(a) at least one acidic compound containing at least one acidic moiety selected from the group consisting of

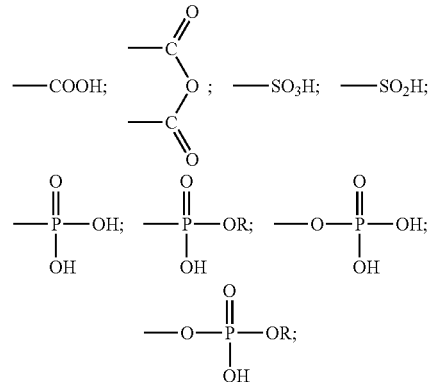

where R is an alkyl or aryl group;
(b) at least one polymerizable monomer without any acidic group where the polymerizable group is selected from the group consisting of an acrylate, a methacrylate and a vinyl group;
(c) at least one finely divided filler;
(d) a reducing agent; and
(e) an oxidizing agent;
and providing instructions for mixing the two pastes immediately prior to application where the ratio of a first paste containing (a) or a higher concentration of (a) to a second paste not containing (a) or containing a lower concentration of (a) is greater than 1:1 (by volume). The method also includes mixing the two pastes and applying the mixed composition to a dental substrate.

46 Claims, No Drawings

METHODS OF USING TWO-PART SELF-ADHERING DENTAL COMPOSITIONS

FIELD OF THE INVENTION

The invention relates generally to methods of preparing, packaging and using a two-part paste/paste self-adhering dental composition, resulting in a more convenient dental procedure and improved adhesion to various dental substrates.

BACKGROUND OF THE INVENTION

The traditional procedure for bonding an indirect restoration, such as an inlay, onlay, or crown to a tooth structure is rather cumbersome. First the carious dentition is removed. The tooth is etched with an acidic etchant to remove the smear layer on the tooth surface, and the tooth is then coated with a thin layer of an acidic primer. The base and catalyst of a cement is mixed and applied to the bonding surface of the indirect restoration, and the restoration is then seated onto the primed tooth surface.

Cement hardening may be effected by self-curing by incorporating a self-cure initiator system, or by the combination of self-curing and photo-curing by using a photo-initiator. When metal is involved in the restorative material, such as a porcelain fused to a metal (PFM) crown, an efficient self-curing cement is needed because it is difficult for light to penetrate the restorative material and reach the cement with sufficient intensity to achieve adequate photo-curing.

The bonding procedure may be simplified by using a self-etching primer, eliminating the etch step, and thus accomplishing etching and priming in one step. The bonding procedure is simplified into the steps of applying a self-etching primer to the tooth and then applying a cement to the restoration material.

To further simplify the bonding procedure, it would be highly desirable to combine the steps of etching, priming, and cementing into one step. This would significantly shorten the chair time for certain restorative procedures. This would also significantly reduce the possibility for errors involved in the restorative procedure because only one step cementation would be involved.

Great difficulties, however, are encountered when combining the ingredients necessary to fulfill the functions of etching, priming, and cementing. For example, acidic compounds are used as an etchant or an etching primer, but the self-cure initiator commonly used in a resin cement is not effective under strongly acidic environments. The self-cure initiator system currently used by most manufacturers to effect self-curing of a resin cement comprises benzoyl peroxide and an aromatic tertiary amine. Two problems arise with use of this system. First, the aromatic tertiary amine loses its effectiveness immediately upon contact with a moderate or strong acid. Second, benzoyl peroxide is not very stable in acidic environments, quickly loses its potency and, therefore, has a rather short shelf-life. As a result, when a self-etching primer is incorporated into a resin cement, the mixed cement fails to harden because the redox initiators lose their potency under acidic environments. A simplified system which reduces or eliminates these difficulties is needed.

SUMMARY OF THE INVENTION

A method is disclosed for providing and using a two-part paste-paste self-adhering dental composition which allows combined etching and priming of a dental surface. The composition may be a restorative composition, an orthodontic composition, or an endodontic composition. A method is also disclosed for using the composition from pre-packaged containers. A first paste contains all the acidic component(s) or a higher concentration of acidic component(s) relative to a second paste. The ratio of the first paste and the second paste in the mixed composition is greater than 1:1 (by volume), and provides enhanced bond strengths to a dental substrate (for example, dentine, enamel, dental metal alloy, porcelain). The composition may be provided in the desired ratio from pre-packaged containers, further simplifying the method for the practitioner and patient.

The method provides a paste/paste two-part self-adhering dental composition comprising
(a) at least one acidic compound containing at least one acidic moiety selected from the group consisting of

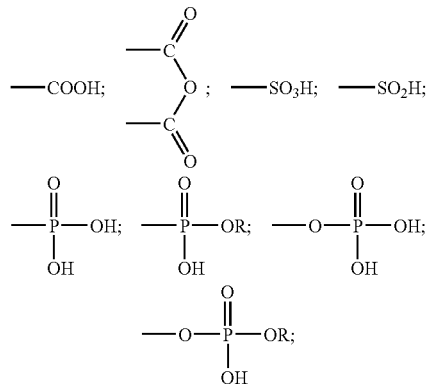

where R is an alkyl or aryl group;
(b) at least one polymerizable monomer without any acidic group where the polymerizable group is selected from the group consisting of an acrylate, a methacrylate and a vinyl group;
(c) at least one finely divided filler;
(d) at least one reducing agent; and
(e) at least one oxidizing agent;

and provides instructions for mixing the two pastes and applying the mixed composition to a dental substrate where the ratio of a first paste containing (a) or a higher concentration of (a) to a second paste not containing (a) or containing a lower concentration of (a) is greater than 1:1 (by volume). The mixed composition is applied to a dental substrate and hardened inside a patient's mouth.

In one embodiment, the first paste comprises
(a) at least one acidic compound containing at least one acidic moiety selected from the group consisting of

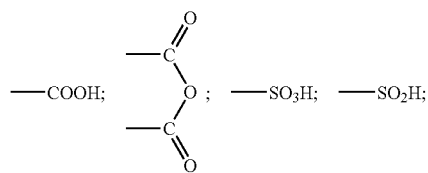

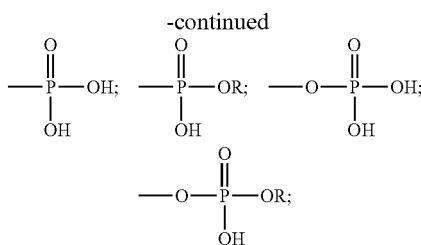

where R is an alkyl or aryl group;
(b) at least one polymerizable monomer without any acidic group where the polymerizable group is selected from the group consisting of an acrylate, a methacrylate and a vinyl group;
(c) at least one finely divided filler;
(d) at least one oxidizing agent;

and the second paste comprises
(e) at least one polymerizable monomer without any acidic group which is either the same as (b) or different from (b) where the polymerizable group is selected from the group consisting of an acrylate, a methacrylate and a vinyl group
(f) at least one finely divided filler which is either the same as (c) or is different from (c);
(g) at least one reducing agent;

with instructions for mixing the two pastes and applying the mixed composition to a dental substrate where the ratio of the first paste to the second paste is greater than 1:1 (by volume).

The two pastes are mixed, and the mixed composition is applied to the dental substrate and hardened inside a patient's mouth. The composition may be pre-packaged, for example, with the first paste in a first syringe and the second paste in a second syringe, where the syringes are two non-joining individual syringes or one dual-syringe assembly. The internal barrel cross-section area of the first syringe containing the first paste to the second syringe containing the second paste is greater than 1:1 (by volume). In alternative embodiments, it may be in the range of about 2:1 (by volume) to about 10:1 (by volume). A dual-syringe assembly may have a static mixer with an exit opening attached to exit openings of the dual-syringe to dispense a substantially homogeneous mixed paste in the desired ratio. Mixing of the two pastes may also be manual, by use of an automated mixing device, or by use of a static mixer.

These and other advantages will be apparent in light of the following figures and detailed description.

DETAILED DESCRIPTION OF THE INVENTION

A method for using a two-part paste/paste acidic self-adhering composition with improved adhesion or bond strength to a dental substrate is disclosed. A two-part paste/paste composition with a base paste containing a substituted thiourea activator, and a catalyst paste containing a tertiary hydroperoxide catalyst, is disclosed in co-pending application Ser. No. 10/440,804 which is expressly incorporated by reference herein in its entirety. The present invention is not limited to these specific base and catalyst pastes, and results in an enhanced bond strength as the total concentration of acidic compound(s) in the mixed composition is increased, or as the ratio of a first paste, containing the acidic compound(s) or a higher concentration of acidic compound(s), relative to a second paste, containing no acidic compound(s) or a lower concentration of acidic compound(s), is increased over 1:1 (by volume).

In one embodiment, the method ensures that the correct ratio of the two pastes is achieved by use of the inventive two-part paste/paste composition from a pre-packaged container, such as a dual syringe assembly, further simplifying the restorative procedures. In another embodiment, the method encompasses automated mixing of the two pastes just prior to being delivered to a dental substrate so that a substantially homogeneous composition is provided.

A first paste contains the acidic compound(s), or a relatively higher concentration of acidic compound(s) compared to a second paste. The second paste contains no acidic compound(s), or a relatively lower concentration of acidic compound(s) compared to the first paste. Mixing the first paste and the second paste at a ratio of greater than 1:1 (by volume) results in improved adhesion to a dentine substrate over that obtained when the amounts of the two pastes are the same, that is, when the two pastes are mixed in a 1:1 (by volume) ratio. Any ratio greater than 1:1 (first paste:second paste, by volume) may be used where curing of the mixed composition is satisfactory to a dental practioner. For example, the ratio may be 1.05:1 (by volume) or 1.1:1 (by volume), the lower limit of which is variable to account for variations in syringe barrels purporting to have identical internal cross-sectional areas when the material is packaged in syringes. In one embodiment, the volume ratio of the first paste containing the acidic compound(s) or a higher concentration of acidic compound(s) to the second paste ranges from greater than 1:1 (by volume) to about 20:1 (by volume). In another embodiment, the volume ratio of the first paste containing the acidic compound(s) or higher concentration of acidic compound(s) to the second paste ranges from 1.05:1 (by volume) to about 20:1 (by volume). In another embodiment, the volume ratio of the first paste containing the acidic compound(s) or higher concentration of acidic compound(s) to the second paste ranges from 1.5:1 (by volume) to about 15:1 (by volume). In another embodiment, the volume ratio of the first paste containing the acidic compound(s) or higher concentration of acidic compound(s) to the second paste is in the range of about 2:1 (by volume) to about 10:1 (by volume). These embodiments are illustrative and not limiting; other ratios greater than 1:1 (by volume) and other ranges may be used.

A convenient restorative procedure can be realized when the composition is pre-packaged, such that the desired ratio is provided upon use. For example, the composition may be packaged in the two syringes of a dual-syringe assembly, two individual non-joined syringes, two tubes, two capsules, one capsule where the two pastes are segregated and do not come in contact with each other, blister packs, etc., as known to one skilled in the art. All the above are examples of pre-packaged containers. A dual syringe assembly, also called a dual cartridge assembly (e.g. Mixpac® from ConProTec Inc. (Salem, N.H.)) contains two syringe barrels of different sizes attached together, and the barrel sizes are selected so that the ratio of the internal cross-sectional area of the larger syringe barrel to that of the smaller syringe barrel is greater than 1:1 (by volume). The paste containing the acidic compound(s) or a higher concentration of acidic compound(s) is packaged in the larger syringe and the paste containing no acidic compound(s) or a lower concentration of acidic compound(s) is packaged in the smaller syringe. When the two pastes are dispensed from the dual syringe assembly, the ratio of the first paste containing the acidic compound(s) or higher concentration of acidic compound(s) to the second paste in the composition is greater than 1:1 (by volume).

The dual-syringe assembly may be fitted with a static mixer/tip so that the two pastes are mixed in the static mixer to result in a homogenous or a substantially homogenous composition which flows out from the tip. The dental practitioner can dispense the homogeneously mixed composition directly to a dental substrate, resulting in significant time savings and convenience in addition to improved adhesion.

The self-adhesive two-part paste/paste dental composition contains the following components:

(a) at least one acidic compound containing at least one acidic moiety selected from the group consisting of

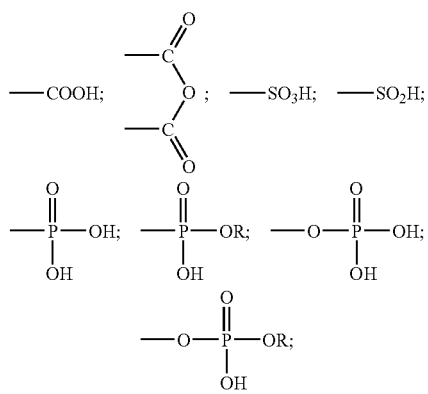

where R is an alkyl or aryl group;

(b) at least one polymerizable monomer without any acidic group where the polymerizable group is selected from the group consisting of an acrylate, a methacrylate and a vinyl group;

(c) at least one finely divided filler;

(d) at least one reducing agent; and (e) at least one oxidizing agent.

The components are formulated as two pastes. The first paste may contain all of the acidic compound(s) (a), in which case the second paste will not contain (a). Alternatively, the first paste may contain a higher concentration of (a) relative to the second paste, in which case the second paste will contain a lower concentration of (a) relative to the first paste. The two pastes are mixed just prior to application, as known to one skilled in the art, so that the first paste containing the acidic compound(s) or a higher concentration of acidic compound(s) and the second paste in the composition are in a ratio greater than 1:1 (by volume). The mixed composition is applied to a dental substrate and hardened inside the patient's mouth. Hardening may be by self-curing (without a photo-initiator) or by the combination of self-curing and photo-curing (with a photo-initiator).

The composition has a bond strength to the dentine substrate of at least 3 MPa. In one embodiment, the bond strength is at least 5 MPa. In another embodiment the bond strength is at least 6 MPa. In the inventive method, an increase in the ratio yields an increase in the bond strength. For example, providing a composition in which the first paste:second paste ratio is 5:1 (by volume) will, upon curing, result in a greater bond strength than a composition in which the first paste:second paste ratio is 1.5:1 (by volume).

One or more additional components may optionally be included in the inventive composition. The additional components include a photo-initiator, a solvent, and/or a stabilizer. They may be incorporated into either the first paste, or the second paste, or into both pastes.

For component (a), any acidic compound with at least one acidic group selected from the group consisting of the following can be used.

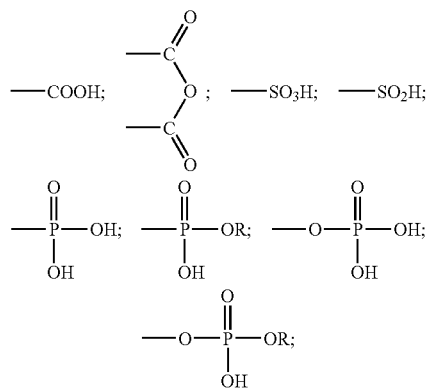

where R is an alkyl or aryl group.

Examples include, but are not limited to, maleic acid, itaconic acid, methacrylic acid, acrylic acid, tartaric acid, ethylenediaminetetraacetic acid (EDTA), EDTA salt, citric acid, a homopolymer or copolymer of an α,β-unsaturated carboxylic acid such as poly(acrylic acid), copolymer of acrylic acid such as poly(acrylic acid-maleic acid) copolymer or poly(acrylic acid-itaconic acid) copolymer or poly(acrylic acid-maleic acid-itaconic acid) copolymer, polymerizable homopolymer or copolymer of an α,β-unsaturated carboxylic acid such as (meth)acrylated poly (acrylic acid) {(meth)acrylated=acrylated or methacrylated}, (meth)acrylated poly(acrylic acid) copolymer such as (meth)acrylated poly(acrylic acid-maleic acid) copolymer or (meth)acrylated poly(acrylic acid-maleic acid-itaconic acid) copolymer, maleic anhydride, trimellitic anhydride, 4-META (4-methacryloxyethyltrimellitic anhydride), any addition product of mono- or di-anhydride compound with a hydroxyalkylmethacrylate compound such as PM-HEMA (addition product of pyromellitic acid anhydride and 2-hydroxyethyl methacrylate), PM-GDM (addition product of pyromellitic acid anhydride and glycerol dimethacrylate), BTDA-HEMA (addition product of 3,3',4,4'-benzophenonetetracarboxylic dianhydride and hydroxyethyl methacrylate), and PA-HEMA (addition product of phthalic anhydride and hydroxyethyl methacrylate), MA-GDM (addition product of maleic anhydride and glycerol dimethacrylate), sulfuric acid, alkyl sulfonic acid, aromatic sulfonic acid, alkyl sulfinic acid, aromatic sulfinic acid, phosphoric acid, pyrophosphoric acid, monoalkyl phosphate, dialkyl phosphate, aryl alkyl phosphate, aryl phosphate, phenyl-P (phenyl methacryloxyethyl phosphate), GDM-P (glyceryldimethacrylate phosphate), PENTA-P (pentaerithritol triacrylate phosphate), MDP (methacryloyloxydecyl phosphate), HEMA-P (hydroxyethylmethacrylate phosphate), and bis(HEMA)-P {bis(hydroxyethylmethacrylate) phosphate}, and a combination thereof.

In specific embodiments, acidic compounds are those having at least one acidic group and at least one ethylenically unsaturated moiety selected from the group consisting of an acrylate, a methacrylate, and a vinyl group, so that it can copolymerize with other monomers. Examples of acidic compounds having at least one acidic group and at least one ethylenically unsaturated moiety include, but are not limited to, methacrylated poly(acrylic acid), methacrylated poly(acrylic acid) copolymer such as methacrylated poly(acrylic acid-maleic acid) copolymer and methacrylated poly(acrylic acid-maleic acid-itaconic acid) copolymer, 4-META, PM-GDM, PM-HEMA, BTDA-HEMA, PA-HEMA, MA-GDM, phenyl-P, GDM-P, PENTA-P, MDP, HEMA-P, and bis(HEMA)-P. In other embodiments, acidic compounds are those having at least one phosphate group and at least one ethylenically unsaturated moiety selected from the group consisting of an acrylate, a methacrylate, and a vinyl group, so that it can copolymerize with other monomers. Examples of acidic compounds having at least one phosphate group and at least one ethylenically unsaturated moiety include, but are not limited to, phenyl-P, GDM-P, PENTA-P, MDP, HEMA-P, and bis(HEMA)-P.

In one embodiment, the concentration of the total acidic compound or compounds is at least 10% (w/w) in the overall composition (excluding filler and solvent). In another embodiment, the concentration of the total acidic compound or compounds is at least 15% (w/w) in the overall composition (excluding filler and solvent). In another embodiment, the concentration of the total acidic compound or compounds is at least 20% (w/w) in the overall composition (excluding filler and solvent).

For component (b), at least one polymerizable monomer without any acidic group can be used. A polymerizable monomer includes any monomer having at least one ethylenically unsaturated moiety selected from the group consisting of an acrylate, a methacrylate, and a vinyl group. In specific embodiments, the ethylenically unsaturated group is selected from acrylate and methacrylate groups. Examples of the polymerizable monomer include, but are not limited to, the following: hydroxyethyl (meth)acrylate {(meth)acrylate=acrylate or methacrylate}, hydroxypropyl (meth)acrylate, hydroxybutyl (meth)acrylate, glycerol di(meth)acrylate, glycerol mono(meth)acrylate, methyl (meth)acrylate, ethyl (meth)acrylate, propyl (meth)acrylate, butyl (meth)acrylate, hexyl (meth)acrylate, octyl (meth)acrylate, lauryl (meth)acrylate, decyl (meth)acrylate, tridecyl (meth)acrylate; 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth)acrylate (TEGDMA), tetraethyleneglycol di(meth)acrylate, polyethyleneglycol mono-(meth)acrylate, polyethyleneglycol di-(meth)acrylate, polypropyleneglycol mono-(meth)acrylate, polypropyleneglycol di-(meth)acrylate, polytetramethyleneglycol mono-(meth)acrylate, polytetramethyleneglycol di-(meth)acrylate, hexanediol di(meth)acrylate, trimethylolpropane tri(meth)acrylate, ethoxylated trimethylolpropane tri(meth)acrylate, UDMA (reaction product of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated bisphenol A dimethacrylate (EBPADMA-n where n=total number of moles of ethylene oxide in the molecule, as only one example, n=2–20 units), tetrahydrofurfuryl (meth)acrylate, or mixtures thereof.

For component (c), one or more filler can be incorporated into the composition. These provide enhancement to the mechanical properties, reduction in polymerization shrinkage, improved rheological properties, and increased radiopacity for easy detection of gaps or voids. Examples of fillers include, but are not limited to, inorganic metal, salt, oxide, nitride, silicate glass, aluminosilicate glass, aluminoborosilicate glass, fluoroaluminosilicate glass, quartz, colloidal silica, precipitated silica, zirconia-silica, polymeric filler, polymerized composite filler with inorganic particles, and combinations of these. In one embodiment, inorganic fillers for increased x-ray contrast ability include metals, salts, oxides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these. Examples include barium sulfate, silver, strontium fluoride, barium fluoride, ytterbium fluoride, ytrium fluoride, barium tungstate, zinc oxide, bismuth(III) oxide, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, etc. Fumed silica, colloidal silica, or precipitated silica can also be incorporated to improve the dispersion of the filler as well as the rheological and handling properties of the material. Examples of colloidal silicas are Aerosil series such as OX-50, OX-130, and OX-200 silica sold by Degussa (Ridgefield Park, N.J.), and Cab-O-Sil M5 and Cab-O-Sil TS-530 silica sold by Cabot Corp (Tuscola, Ill.). The filler also includes nanoparticles such as those obtained through a sol-gel process. Examples include those disclosed in U.S. Pat. Nos. 4,567,030 and 5,609,675, the disclosure of each expressly incorporated by reference herein in its entirety. Mixtures of different fillers can be used.

For inorganic fillers, the surface of the filler may be treated or coated with a coupling agent such as γ-methacryloyloxypropyltrimethoxy-silane (MPTMS). This enhances the interfacial bonding between the filler and resin matrix, and improves mechanical properties. In various embodiment, the mean particle size of the filler is less than 50 μm, or the mean particle size of the filler is less than 10 μm. The concentration range of total filler(s) is in the range of about 0.5% by weight to about 90% by weight. The specific concentration range depends on the application. For adhesive applications, the concentration of filler is in the range of about 0.5% by weight to about 70% by weight. For cement applications, the concentration of filler is in the range of about 15% by weight to about 80% by weight. For filling materials, the concentration of filler is in the range of about 30% by weight to about 90% by weight.

For component (d), any reducing agent can be used. The reducing agents include, but are not limited to, aromatic sulfinate salt, aliphatic sulfinate salt, thiourea, substituted thiourea, Fe(II) salt, Cu(I) salt, Co(II) salt, ascobic acid, ascobic acid derivative and salt, barbituric acid, barbituric acid derivative and salt, thiobarbituric acid, and thiobarbituric acid derivative and salt. In one embodiment, the reducing agent is a substituted thiourea. Substituted thioureas include, but are not limited to, 1-(2-pyridyl)-2-thiourea, 1-acetyl-2-thiourea, and 1-(2-tetrahydrofurfuryl)-2-thiourea. The concentration of total reducing agent or agents is in the range of about 0.01% (w/w) to about 10.0% (w/w) of the overall composition. In one embodiment, the concentration of total reducing agent(s) is in the range of about 0.1% (w/w) to about 3.0% (w/w) of the overall composition.

For component (e), any oxidizing agent can be used. Oxidizing agents include, but are not limited to, a tertiary hydroperoxide compound with at least one hydroperoxide group attached to at least one tertiary carbon, Cu(II) salt such as Cu(II) acetylacetonate, Cu(II) benzoylacetonate, and Cu(II) cyclohexylbutyrate, Fe(III) salt such as $FeCl_3$, Fe(III) benzoyl acetonate, and Fe(III) cyclohexylbutyrate, Co(III)

salt, persulfate salt, permanganate salt, and combinations of these. In one embodiment, tertiary hydroperoxide compounds are used. Examples of tertiary hydroperoxide compounds include, but are not limited to, t-butyl hydroperoxide, t-amyl hydroperoxide, p-diisopropylbenzene hydroperoxide, cumene hydroperoxide, pinane hydroperoxide, p-methane hydroperoxide, and 1,1,3,3-tetramethylbutyl hydroperoxide. In one embodiment, the concentration of total oxidizing agent or agents is in the range of about 0.01% (w/w) to about 10.0% (w/w) of the overall composition. In another embodiment, the concentration of total oxidizing agent or agents is in the range of about 0.1% (w/w) to about 5.0% (w/w) of the overall composition.

The reducing agent(s) and oxidizing agent(s) form a self-cure initiator system to cure or harden the mixed composition. That is, when the two pastes are mixed, the reducing agent(s) and the oxidizing agent(s) come into contact with each other and a redox reaction takes place. The redox reaction generates free radicals and initiates polymerization of monomers, leading to curing or hardening of the mixed composition.

In one embodiment, the reducing agent(s) and oxidizing agent(s) are incorporated into separate pastes. In another embodiment, one or both of them is microencapsulated and they are both in the same paste or in different pastes. Microencapsulation may be achieved by methods known to one skilled in the art, for example using water soluble or water insoluble encapsulants. In one embodiment, the reducing agent(s) is incorporated into the paste containing no acidic compound(s) or a lower concentration of acidic compound(s). In another embodiment, the reducing agent is microencapsulated and may be incorporated into either paste.

In one embodiment, a photo-initiator can be utilized to make the composition dual-curable, i.e. both self-curable (in the absence of light) and photo-curable. Examples of photo-initiators include, but are not limited to, benzoin, benzoin ethers and esters, 2,2-diethoxy acetophenone, diketone compounds such as camphorquinone and 1-phenyl-1,2-propanedione, monoacylphosphine oxide, bisacylphosphine oxide as disclosed in U.S. Pat. No. 4,792,632, which is expressly incorporated by reference herein in its entirety, diaryliodonium salt, triarylsulfonium salt, and a mixture of photo-initiators. Additionally, an activator can be used together with a photo-initiator to enhance curing efficiency. Activators include tertiary amine and sulfinate compounds. Examples of activators include, but are not limited to, ethyl 4-(N,N-dimethylamino) benzoate, 2-(ethylhexyl)-4-(N,N-dimethylamino) benzoate, N,N-dimethylaminoethyl methacrylate, N,N-dimethylaminophenethyl alcohol, sodium benzenesulfinate, and sodium toluenesulfinate. In one embodiment, a photo-initiator system includes the combination of camphoroquinone and a tertiary amine such as ethyl 4-(N,N-dimethylamino) benzoate, 2-(ethylhexyl)4-(N,N-dimethylamino) benzoate, N,N-dimethylaminoethyl methacrylate, and N,N-dimethylaminophenethyl alcohol. The components of the photo-initiator system can be incorporated into the first paste, the second paste, or both pastes.

In one embodiment, a solvent can also be incorporated into the composition. Useful solvents include water, methanol, ethanol, isopropanol, acetone, methyl ethyl ketone, ethylene glycol, and glycerin. The solvent can be incorporated into the first paste, the second paste, or both pastes.

Other ingredients can also be incorporated into the inventive composition, such as colorants, stabilizers, UV absorbers, and antimicrobial additives. Colorants are used to achieve desired shades and can be inorganic pigments or organic dyes. Stabilizers are polymerization inhibitors to improve the shelf stability of the restorative material. Stabilizers include 2,6-di-(tert-butyl)-4-methylphenol (BHT) and 4-methoxyphenol (MEHQ). UV absorbers improve the color stability of the restorative material upon exposure to UV light. An example of UV absorber is 2-hydroxy-4-methoxybenzophenone (UV-9).

The above described initiator, using the combination of a reducing agent and an oxidizing agent, is used in a two-part paste/paste self-adhering self-cure dental composition (i.e. curing without the activation of light), or a dual-cure dental composition (both self-cure and photo-cure) when a photo-initiator is also included. When the two pastes are mixed and self-cured (without photo-curing), the mixed composition will set (or harden) within about 30 minutes. In embodiments, setting occurs within about 20 minutes from the start of mixing, or within about 10 minutes from the start of mixing.

An example of a paste/paste two-part self-adhering dental composition is a first paste containing an acidic compound(s), an oxidizing agent(s), one or more non-acidic polymerizable monomers, and one or more finely divided fillers, and a second paste containing one or more polymerizable monomers, a reducing agent(s), and one or more finely divided fillers. A photo-initiator may also be incorporated. The acidic compound may be a polymerizable monomer. The two parts are mixed just prior to application, applied to a dental substrate, and hardened inside a patient's mouth by self-curing or by the combination of self-curing and light-curing. In one embodiment, at least one filler in the second paste is a reactive filler or ion-leachable filler, such as a metal oxide or a fluoroaluminosilicate glass. In another embodiment, at least one acidic compound of the first paste is an acidic polymer such as a homopolymer or copolymer of an $\alpha,\beta$-unsaturated carboxylic acid; or a polymerizable acidic polymer such as (meth)acrylated homopolymer or copolymer of an $\alpha,\beta$-unsaturated carboxylic acid. A solvent can be incorporated into either paste or both pastes. In one embodiment, water is incorporated into the first paste. If either or both the reducing agent and the oxidizing agent is microencapsulated, both the reducing agent and the oxidizing agent can be incorporated into either paste, and may be incorporated into the same paste. In one embodiment, all the acidic compound(s) are incorporated into the first paste. In another embodiment, a small amount of acidic compound(s) is incorporated into the second paste such that it does not cause the instability of the reducing agent, and the remaining acid compound(s) is incorporated into the first paste.

The inventive composition is useful in formulating restorative materials such as a filling material, a cement, a base/liner, a pit/fissure sealant, or an adhesive. It is also useful in formulating orthodontic materials such as an orthodontic adhesive and cement. It is also useful in formulating endodontic materials such as an endodontic adhesive, a cement for post cementation, or an endodontic sealing or filling material.

The invention also includes a method for preparing a two-part paste/paste self-adhering dental composition. The two pastes are mixed just prior to application such that the ratio in the mixed composition of the first paste containing the acidic compound(s) or a higher concentration of acidic compound(s) to the second paste is greater than 1:1 (by volume). The mixed composition is applied to a dental substrate such as dentine, enamel, dental metal alloy and porcelain, and the mixture is hardened either by self-curing or by the combination of self-curing and photo-curing. In various embodiments, the bond strength of the mixed composition to an unetched and unprimed dentine substrate is at least 3 MPa, at least 5 MPa, or at least 6 MPa.

Mixing of the two pastes can be achieved by any mixing means. For example, the pastes may be mixed manually using a spatula, a mixing stick, etc. They may be mixed using an automated mixing device, such as an amalgamator or a Rotomix™ (3M ESPE, St. Paul, Minn.). Mixing may also be accomplished by a static mixer when using a dual syringe assembly. The use of an automated mixing device or a static mixer can result in a significant time saving for the dental practitioner. Mechanical properties of the mixed composition are also enhanced when using an automated mixer or static mixer because air bubbles are minimized, compared to hand mixing.

The two pastes in the disclosed ratio may be pre-packaged in a single dose form. In this form, the pastes are packaged separately and, in use, the contents are mixed. For example, the two pastes in the desired ratio are packaged within a single capsule without contacting each other. The capsul is then placed on the amalgamator or Rotomix™ and the pastes are automatically mixed. The packaging material, along with any remaining paste, is discarded. Such a single use packaging device eliminates a dental practitioner's concern of cross-contamination.

The two pastes may be packaged in two separate syringes. Any syringe size may be selected as long as the ratio of the cross-sectional area of the exit opening of the first syringe compared to the exit opening of the second syringe is greater than 1:1 (by volume). In this embodiment, when an equal length of each paste is dispensed, the desired ratio of the two pastes is obtained. Alternatively, the internal cross-sectional areas of the syringe barrels may differ such that, when the pastes are dispensed, the desired ratio of the first and second pastes is obtained. In another embodiment, any size syringe may be selected to contain either paste, with a metering device controlling the paste dispensed such that the desired ratio is obtained.

The two pastes may be packaged in a dual-syringe assembly. Each syringe in the assembly has an exit opening. The syringe barrels have different internal cross-sectional areas, with the ratio of the internal cross-sectional areas of the first syringe barrel to the second syringe barrel of greater than 1:1 (by volume). Dispensing the pastes by applying pressure to the plunger results in a composition where the ratio of the first and second paste is greater than 1:1 (by volume). A static mixer may be attached to the two exit openings of the assembly. The two pastes are mixed in a static mixer to achieve a substantially homogenous composition, and the mixed composition flows out from the exit opening.

Much simplified restorative procedures and significant time savings result when the acidic self-adhering dental composition is used to bond to dental substrates such as dentine, enamel, dental alloys and porcelain because etching and/or priming of the substrate is unnecessary. Restorative procedures are further simplified when a dual syringe assembly fitted with a static mixer is used. The self-adhering dental composition incorporating the above described self-cure initiator can be used as a dental filling material, cement, liner/base, a pit/fissure sealant, or an adhesive. The inventive composition may be used as a restorative dental composition, an endodontic composition, and an orthodontic composition. When used to bond to a dental substrate, etching and priming of the substrate is optional.

The following examples illustrate how the current invention may be applied and do not limit the scope of the invention.

EXAMPLES

Abbreviations for materials used in all examples.

| | |
|---|---|
| Barium Glass: | bariumaluminoborosilicate filler that has an mean particle size of 1.0 micron and its surface was treated with MPTMS |
| BHT: | 2,6-di-(tert-butyl)-4-methylphenol |
| Bis-GMA: | 2,2-bis[4-(2-hydroxy-3-methacryloylpropoxy)-phenyl]-propane |
| CHP: | cumene hydroperoxide |
| CQ: | camphoroquinone |
| EDMAB: | ethyl 4-(N,N-dimethylamino) benzoate |
| ETMPTA: | ethoxylated trimethylolpropane triacrylate with 3 moles of ethylene oxide |
| GDM: | glyceryldimethacrylate |
| GDM-P: | glyceryldimethacrylate phosphate |
| HEMA: | hydroxyethyl methacrylate |
| MEHQ: | 4-methoxyphenol |
| MPTMS: | γ-methacryloyloxypropyltrimethoxysilane |
| PTU: | 1-(2-pyridyl)-2-thiourea |
| Sr/Zn FAS Glass: | strontiumzincfluoroaluminosilicate glass that has a mean particle size of 4.0 microns and its surface was treated with MPTMS |
| ST-OX-50: | fumed silica OX-50 surface treated with MPTMS |
| TMBHP: | 1,1,3,3-tetramethylbutyl hydroperoxide |
| TS-530: | surface treated fumed silica or colloidal silica sold by Cabot Corp. |
| UDMA: | reaction product of 2-hydroxyethyl methacrylate with 2,4,4-trimethylhexane diisocynate |

Example 1

In making all the pastes in this example, first all the monomers and any ingredients soluble in the resin mixture were mixed together to make a homogeneous liquid mixture, and then the fillers (TS-530, ST-OX-50, Sr/Zn FAS Glass, or Barium Glass) were blended into the liquid mixture to make the paste.

A paste/paste two-part self-adhering dental cement composition was prepared and tested as an example. A first paste using 1,1,3,3-tetramethylbutyl hydroperoxide (TMBHP)/cumene hydroperoxide (CHP) oxidizing agents and acidic monomers GDM-P, and a second paste using 1-(2-pyridyl)-2-thiourea (PTU) as the reducing agent, was made.

| First (Catalyst) Paste | |
|---|---|
| BisGMA | 3.23 |
| GDM-P | 16.96 |
| HEMA | 7.27 |
| GDM | 4.85 |
| BHT | 0.05 |
| TMBHP | 0.57 |
| CHP | 0.57 |
| TS530 | 2.00 |
| ST-OX-50 | 3.23 |
| Barium Glass | 61.28 |

| Second (Base) Paste | |
|---|---|
| UDMA | 22.00 |
| ETMPTA | 5.50 |
| CQ | 0.17 |
| MEHQ | 0.010 |
| EDMAB | 0.28 |

-continued

| | Second (Base) Paste |
|---|---|
| PTU | 0.54 |
| TS-530 | 3.00 |
| ST-OX-50 | 4.80 |
| Sr/Zn FAS Glass | 63.70 |

When mixed at 1:1 ratio (by volume), the above first and second pastes had a set time of 3 minutes 50 seconds (3'50").

A bonding strength test to dentine substrate was conducted using the above first and second pastes (self-adhering cement). The dentine surface was polished with 600 grit SiC paper. The mixed pastes were directly applied to the dentine surface and the bond strength was determined on an Instron Universal Tester (Model 4467) in shear mode after 24 hours conditioning in a high humidity chamber (85%–90% relative humidity) kept at 37° C. The curing was self-cure only (no light-curing). The mixed self-adhering cement paste had a bond strength to an unetched and unprimed dentine substrate of 4.48 MPa (average of 7 specimens).

Example 2

The two pastes from Example 1 were mixed at 4:1 (first paste:second paste) ratio (by volume). The set time was 5'40". Bonding strength of the mixed composition was determined as in Example 1. With the two pastes mixed at a 4:1 (by volume) ratio, the bond strength to an unetched and unprimed dentine substrate was 8.87 MPa (average of 6 specimens) in self-cure mode. This is almost double the bond strength of that obtained over that in Example 1 using a 1:1 (by volume) ratio.

The above examples clearly illustrate the usefulness of the inventive method. The inventive composition may be used as a dental restorative composition, an endodontic composition, and an orthodontic composition. Useful restorative compositions include a dental filling material, a cement, a liner, a base, a pit/fissure sealant, or an adhesive composition. Useful endodontic compositions include an endodontic sealing and/or filling composition for the sealing and filling of a root canal, or an endodontic adhesive or cement for post-cementation. Useful orthodontic compositions include an orthodontic adhesive or cement composition for adhering an orthodontic appliance to tooth surfaces.

Other variations or embodiments of the invention will also be apparent to one of ordinary skill in the art from the above descriptions and examples. Thus, the forgoing embodiments are not to be construed as limiting the scope of this invention.

The invention claimed is:

1. A method for providing a dental composition comprising
   providing a paste/paste two-part self-adhering dental composition, a first paste comprising water and
   (a) at least one acidic compound comprising a homopolymer/copolymer of an α,β-unsaturated carboxylic acid;
   (b) at least one polymerizable monomer without any acidic group where the polymerizable group is selected from the group consisting of an acrylate, a methacrylate and a vinyl group;
   (c) at least one finely divided filler having a mean particle size of less than 50 microns;
   (d) at least one oxidizing agent;
   and a second paste comprising
   (e) at least one polymerizable monomer without any acidic group which is either the same as (b) or different from (b) where the polymerizable group is selected from the group consisting of an acrylate, a methacrylate and a vinyl group;
   (f) at least one finely divided filler which is either the same as (c) or is different from (c);
   (g) at least one reducing agent;
   providing instructions for mixing the two pastes and applying the mixed composition to a dental substrate wherein the ratio of the first paste to the second paste is greater than 1:1 (by volume).

2. The method of claim 1 wherein the composition is mixed, applied to the dental substrate, and hardened inside a patient's mouth.

3. The method of claim 1 wherein the composition further comprises at least one component selected from the group consisting of a photo-initiator, a stabilizer, a solvent, and combinations thereof.

4. The method of claim 1 wherein the filler is selected from the group consisting of inorganic metal, salt, oxide, nitride, silicate glass, aluminosilicate glass, aluminoborosilicate glass, fluoroaluminosilicate glass, quartz, colloidal silica, precipitated silica, zirconia-silica, polymeric filler, polymerized composite filler with inorganic particles, and combinations thereof.

5. The method of claim 4 wherein the metal, salt, oxide, silicate glass, aluminosilicate glass, aluminoborosilicate glass, and fluoroaluminosilicate glass contains an element selected from the group consisting of Sr, Y, Zr, Ba, La, Hf, Zn, Bi, W, a rare earth metal, and combinations thereof.

6. The method of claim 3 wherein the solvent is selected from the group consisting of water, acetone, methanol, ethanol, isopropanol, ethylene glycol, glycerin, or combinations thereof.

7. The method of claim 1 wherein the acidic homopolymer/copolymer is a polymerizable homopolymer/copolymer with at least one ethylenically unsaturated group selected from the group consisting of an acrylate, a methacrylate, and a vinyl group.

8. The method of claim 1 wherein the oxidizing agent is selected from the group consisting of a tertiary hydroperoxide compound with at least one hydroperoxide group attached to at least one tertiary carbon, Cu(II) salt, Fe(III) salt, Co(III) salt, persulfate salt, permanganate salt, and combinations thereof.

9. The method of claim 1 wherein the oxidizing agent is a tertiary hydroperoxide selected from the group consisting of t-butyl hydroperoxide, t-amyl hydroperoxide, p-diisopropylbenzene hydroperoxide, cumene hydroperoxide, pinane hydroperoxide, p-methane hydroperoxide, 1,1,3,3-tetramethylbutyl hydroperoxide, and combinations thereof.

10. The method of claim 1 wherein the reducing agent is selected from the group consisting of aromatic sulfinate salt, aliphatic sulfinate salt, thiourea, substituted thiourea, ascorbic acid, ascorbic acid derivative and salt, Fe(II) salt, Cu(I) salt, Co(II) salt, barbituric acid, barbituric acid derivative, thiobarbituric acid, thiobarbituric acid derivative and salt, and combinations thereof.

11. The method of claim 1 wherein the reducing agent is a substituted thiourea selected from the group consisting of 1-(2-pyridyl)-2-thiourea, 1-(2-tetrahydrofufuryl)-2-thiourea, and 1-acetyl-2-thiourea.

12. The method of claim 1 wherein the dental composition is selected from the group consisting of a restorative composition, an orthodontic composition, or an endodontic composition.

13. The method of claim 1 wherein the dental composition is selected from the group consisting of a dental filling composition, a cement composition, a base/liner composition, a pit/fissure sealant composition, and an adhesive composition.

14. The method of claim 1 wherein the paste/paste two-part self-adhering dental composition is provided from a prepackaged container(s).

15. The method of claim 1 wherein the first paste is in a first syringe barrel and the second paste is in a second syringe barrel, the first and second syringes selected from group consisting of two non-joining individual syringes and one dual-syringe assembly.

16. The method of claim 15 wherein the ratio of an internal cross-sectional area of the first syringe barrel containing the first paste to the second syringe barrel containing the second paste is in the range of 1.05:1 (by volume) to about 20:1 (by volume).

17. The method of claim 16 wherein the relative ratio is in the range of about 2:1 (by volume) to about 10:1 (by volume).

18. The method of claim 15 wherein a static mixer with an exit opening is attached to exit openings of the dual-syringe to dispense a substantially homogeneous mixed paste.

19. The method of claim 1 wherein the first and second pastes are packaged in single-dose form without contact between the first and second pastes and the ratio of the first paste to the second paste is in the range between 1.05:1 (by volume) to about 20:1 (by volume).

20. The method of claim 1 wherein mixing is by a method selected from the group consisting of manual mixing, use of an automated mixing device, and use of a static mixer.

21. The method of claim 1 wherein the ratio of the first paste to the second paste is in the range between about 2:1 (by volume) to about 10:1 (by volume).

22. The method of claim 1 wherein the mixed composition has a bond strength to an unetched and unprimed dental substrate of at least 3 MPa.

23. The method of claim 1 wherein a total concentration of the at least one acidic compound excluding the filler is at least 10% (w/w).

24. A method for providing a dental composition comprising
providing a paste/paste two-part self-adhering dental composition, a first paste comprising
(a) at least one acidic compound selected from the group consisting of
(i) an acidic polymerizable monomer containing at least one polymerizable group selected from the group consisting of an acrylate, a methacrylate, and a vinyl group, and at least one acidic moiety selected from the group consisting of

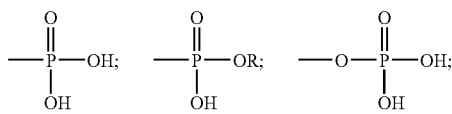

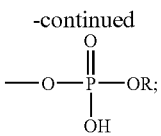

where R is an alkyl or aryl group;
(ii) an addition product of a mono- or di-anhydride compound with a hydroxyalkyl(meth)acrylate compound; and
(iii) 4-(meth)acryloxyethyltrimellitic anhydride;
(b) at least one polymerizable monomer without any acidic group where the polymerizable group is selected from the group consisting of an acrylate, a methacrylate and a vinyl group;
(c) at least one finely divided filler having a mean particle size of less than 50 microns;
(d) at least one oxidizing agent;
and a second paste comprising
(e) at least one polymerizable monomer without any acidic group which is either the same as (b) or different from (b) where the polymerizable group is selected from the group consisting of an acrylate, a methacrylate and a vinyl group;
(f) at least one finely divided filler which is either the same as (c) or is different from (c); and
(g) at least one reducing agent;
providing instructions for mixing the two pastes and applying the mixed composition to a dental substrate wherein the ratio of the first paste to the second paste is greater than 1:1 (by volume).

25. The method of claim 24 wherein the composition is mixed, applied to the dental substrate, and hardened inside a patient's mouth.

26. The method of claim 24 wherein the composition further comprises at least one component selected from the group consisting of a photo-initiator, a stabilizer, a solvent, and combinations thereof.

27. The method of claim 24 wherein the filler is selected from the group consisting of inorganic metal, salt, oxide, nitride, silicate glass, aluminosilicate glass, aluminoborosilicate glass, fluoroaluminosilicate glass, quartz, colloidal silica, precipitated silica, zirconia-silica, polymeric filler, polymerized composite filler with inorganic particles, and combinations thereof.

28. The method of claim 27 wherein the metal, salt, oxide, silicate glass, aluminosilicate glass, aluminoborosilicate glass, and fluoroaluminosilicate glass contains an element selected from the group consisting of Sr, Y, Zr, Ba, La, Hf, Zn, Bi, W, a rare earth metal, and combinations thereof.

29. The method of claim 26 wherein the solvent is selected from the group consisting of water, acetone, methanol, ethanol, isopropanol, ethylene glycol, glycerin, and combinations thereof.

30. The method of claim 24 wherein the acidic compound is selected from the group consisting of hydroxyethylmethacrylate phosphate (HEMA-P), {bis(hydroxyethylmethacrylate)phosphate}(bis(HEMA)-P), glyceryldimethacrylate phosphate (GDM-P), methacryloyloxydecyl phosphate (MDP), phenyl-P, pentaerithritol triacrylate phosphate (PENTA-P), and combinations thereof.

31. The method of claim 24 wherein the oxidizing agent is selected from the group consisting of a tertiary hyderoxide compound with at least one hydroperoxide group attached to at least one tertiary carbon, Cu(II) salt, Fe(III) salt, Co(III) salt, persulfate salt, permanganate salt, and combinations thereof.

32. The method of claim 24 wherein the oxidizing agent is a tertiary hydroperoxide selected from the group consisting of t-butyl hydroperoxide, t-amyl hydroperoxide, p-diisopropylbenzene hydroperoxide, cumene hydroperoxide, pinane hydroperoxide, p-methane hydroperoxide, 1,1,3,3-tetramethylbutyl hydroperoxide, and combinations thereof.

33. The method of claim 24 wherein the reducing agent is selected from the group consisting of aromatic sulfinate salt, aliphatic sulfinate salt, thiourea, substituted thiourea, ascorbic acid, ascorbic acid derivative and salt, Fe(II) salt, Cu(I) salt, Co(II) salt, barbituric acid, barbituric acid derivative, thiobarbituric acid, thiobarbituric acid derivative and salt, and combinations thereof.

34. The method of claim 24 wherein the reducing agent is a substituted thiourea selected from the group consisting of 1-(2-pyridyl)-2-thiourea, 1-(2-tetrahydrofufuryl)-2-thiourea, and 1-acetyl-2-thiourea.

35. The method of claim 24 wherein the dental composition is selected from the group consisting of a restorative composition, an orthodontic composition, and an endodontic composition.

36. The method of claim 24 wherein the dental composition is selected from the group consisting of a dental filling composition, a cement composition, a base/liner composition, a pit/fissure sealant composition, and an adhesive composition.

37. The method of claim 24 wherein the paste/paste two-part self-adhering dental composition is provided from a prepackaged container(s).

38. The method of claim 24 wherein the first paste is in a first syringe barrel and the second paste is in a second syringe barrel, the first and second syringes selected from group consisting of two non-joining individual syringes and one dual-syringe assembly.

39. The method of claim 38 wherein the ratio of an internal cross-sectional area of the first syringe barrel containing the first paste to the second syringe barrel containing the second paste is in the range of 1.05:1 (by volume) to about 20:1 (by volume).

40. The method of claim 39 wherein the relative ratio is in the range of about 2:1 (by volume) to about 10:1 (by volume).

41. The method of claim 38 wherein a static mixer with an exit opening is attached to exit openings of the dual-syringe to dispense a substantially homogeneous mixed paste.

42. The method of claim 24 wherein the first and second pastes are packaged in single-dose form without contact between the first and second pastes and the ratio of the first paste to the second paste is in the range between about 1.05:1 (by volume) to about 20:1 (by volume).

43. The method of claim 24 wherein mixing is by a method selected from the group consisting of manual mixing, use of an automated mixing device, and use of a static mixer.

44. The method of claim 24 wherein the ratio of the first paste to the second paste is in the range between about 2:1 (by volume) to about 10:1 (by volume).

45. The method of claim 24 wherein the mixed composition has a bond strength to an unetched and unprimed dentine substrate of at least 3 MPa.

46. The method of claim 24 wherein a total concentration of the at least one acidic compound excluding the filler is at least 10% (w/w).

* * * * *

UNITED STATES PATENT AND TRADEMARK OFFICE
CERTIFICATE OF CORRECTION

PATENT NO. : 7,214,726 B2
APPLICATION NO. : 10/621708
DATED : May 8, 2007
INVENTOR(S) : Xuejun Qian It is certified that error appears in the above-identified patent and that said Letters Patent is hereby corrected as shown below:

Col. 1, Line 21, "cement is mixed" should read --cement are mixed--.
Col. 3, Line 25, "vinyl group" should read --vinyl group;--.
Col. 8, Line 24, "Corp" should read --Corp.--
Col. 8, Lines 34-35, "various embodiment," should read --various embodiments,--.
Col. 8, Lines 49-50, "ascobic acid, ascobic acid derivative" should read --ascorbic acid, ascorbic acid derivative--.
Col. 9, Line 54, "2-(ethylhexyl)4-(N," should read --2-(ethylhexyl)-4-(N,--.
Col. 11, Line 19, "capsul" should read --capsule--.
Col. 12, Line 7, "has an mean" should read --has a mean--.
Col. 14, Lines 55-56, "thiourea, ascobic acid" should read --thiourea, ascorbic acid--.
Col. 14, Line 62, "1-(2-tetrahydrofufuryl)" should read --1-(2-tetrahydrofurfuryl)--.
Col. 15, Line 15, "selected from group" should read --selected from the group--.
Col. 17, Lines 12-13, "thiourea, ascobic acid" should read --thiourea, ascorbic acid--.
Col. 17, Line 19, "1-(2-tetrahydrofufuryl)" should read --1-(2-tetrahydrofurfuryl)--.
Cols. 17, Line 35 to Col. 18, Line 1, "selected from group" should read --selected from the group--.

Signed and Sealed this

Eleventh Day of December, 2007

JON W. DUDAS
*Director of the United States Patent and Trademark Office*